US010874118B2

(12) United States Patent
Kim et al.

(10) Patent No.: US 10,874,118 B2
(45) Date of Patent: Dec. 29, 2020

(54) BACILLUS SP. STRAIN WITH IMPROVED PRODUCTIVITY OF FERMENTED SOYBEAN MEAL AND METHOD FOR PRODUCING FERMENTED SOYBEAN MEAL USING THE SAME

(71) Applicant: CJ CHEILJEDANG CORPORATION, Seoul (KR)

(72) Inventors: Taek Beom Kim, Seoul (KR); Song Hui Gwon, Bucheon-si (KR); Bi Na Kim, Anyang-si (KR); Seong Jun Cho, Seoul (KR); Kyung Il Kang, Incheon (KR); Seung Won Park, Yongin-si (KR); Young Ho Hong, Gwangmyeong-si (KR); Min Ju Park, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/111,450

(22) PCT Filed: Jan. 28, 2015

(86) PCT No.: PCT/KR2015/000900
§ 371 (c)(1),
(2) Date: Jul. 13, 2016

(87) PCT Pub. No.: WO2015/115790
PCT Pub. Date: Aug. 6, 2015

(65) Prior Publication Data
US 2017/0020161 A1 Jan. 26, 2017

(30) Foreign Application Priority Data

Jan. 28, 2014 (KR) ........................ 10-2014-0010729

(51) Int. Cl.
| A23K 10/12 | (2016.01) |
| C12R 1/07 | (2006.01) |
| C12N 1/20 | (2006.01) |
| A23K 10/16 | (2016.01) |
| A23K 20/147 | (2016.01) |
| A23K 10/14 | (2016.01) |
| A23K 50/10 | (2016.01) |
| A23L 11/00 | (2016.01) |
| A23K 50/60 | (2016.01) |

(52) U.S. Cl.
CPC ............. *A23K 10/12* (2016.05); *A23K 10/14* (2016.05); *A23K 10/16* (2016.05); *A23K 20/147* (2016.05); *A23K 50/10* (2016.05); *A23K 50/60* (2016.05); *A23L 11/09* (2016.08); *C12N 1/20* (2013.01); *C12R 1/07* (2013.01)

(58) Field of Classification Search
CPC ...... A23K 10/12; A23K 10/14; A23K 20/147; A23K 50/10; C12N 1/20; C12R 1/07

USPC .................................................. 426/46, 460
See application file for complete search history.

(56) References Cited

U.S. PATENT DOCUMENTS

| 6,146,669 A | 11/2000 | Jones et al. | |
| 2010/0143316 A1* | 6/2010 | Hsieh | A01N 63/00 424/93.46 |
| 2011/0230345 A1* | 9/2011 | Snyder | A01N 63/00 504/101 |
| 2011/0274673 A1* | 11/2011 | Kang | A01N 63/00 424/93.46 |
| 2015/0147303 A1* | 5/2015 | Hsieh | A01N 63/00 424/93.46 |

FOREIGN PATENT DOCUMENTS

| KR | 10-2003-0095973 A | 12/2003 |
| KR | 10-0645284 B1 | 11/2006 |
| KR | 10-2009-0093947 A | 9/2009 |
| KR | 10-2011-0027535 A | 3/2011 |
| KR | 10-2013-0005592 A | 1/2013 |
| KR | 101 270 664 B1 | 1/2013 |
| WO | WO 2011/031020 A2 | 3/2011 |
| WO | WO 2012/105805 A2 | 8/2012 |

OTHER PUBLICATIONS

Oleg, N. R. et al. 2004. FEMS Microbiol. Ecolog. 48: 249-259 (Year: 2004).*
Reva, O. N. et al. 2004. FEMS Microbiology Ecology. 48: 249-259. (Year: 2004).*
Extended European Search Report dated Jul. 28, 2017 in connection with related European Patent Application No. EP 15 743 540.5.
D. F. Li, et al., "Transient Hypersensitivity to Soybean Meal in the Early-Weaned Pig", J. Anim. Sci., (1990), 68: 1790-1799, Kansas State University, Manhattan.
Atsuo Goto & Masao Kunioka, "Biosynthesis and Hydrolysis for Poly(γ-glutamic acid) from Bacillus subtilis IF03335", Bioscience, Biotechnology, and Biochemistry, (1992), 56:7, 1031-1035.

(Continued)

Primary Examiner — Hamid R Badr
(74) Attorney, Agent, or Firm — John P. White; Gary J. Gershik

(57) ABSTRACT

The present invention relates to a *Bacillus amyloliquefaciens* K2G strain, which is excellent in removal of anti-nutritional factors and in protease activity, and shows excellent antimicrobial activity against pathogens and reduced productivity of viscous substances, a method for producing a fermented soybean meal using the strain, a fermented soybean meal produced therefrom, and a feed composition including the same. The fermented soybean meal prepared by *Bacillus amyloliquefaciens* K2G strain according to the present invention has few anti-nutritional factors such as trypsin inhibitors, soybean oligosaccharides, and polysaccharides, a high content of crude proteins, and high protein solubility, and also consists of small-sized peptides digestible by livestock due to low-molecularization, thereby being effectively used as a high-quality vegetable protein feed having excellent absorption rate and feed efficiency.

8 Claims, 4 Drawing Sheets

Specification includes a Sequence Listing.

(56) References Cited

OTHER PUBLICATIONS

A. Aburto, et al., "Strategies for Utilizing Overprocessed Soybean Meal: I. Amino Acid Supplementation, Choline Content, and Matabolizable Energy", J. Appl. Poultry Res., (1998), 7:189-195.
C. M. Parsons, et al., "Soybean Protein Solubility in Potassium Hydroxide: an In Vitro Test of In Vivo Protein Quality" J. Anim. Sci., (1991), 69:2918-2929.
International Search Report in connection with PCT International Application No. PCT/KR2015/000900.

\* cited by examiner

[FIG. 1]
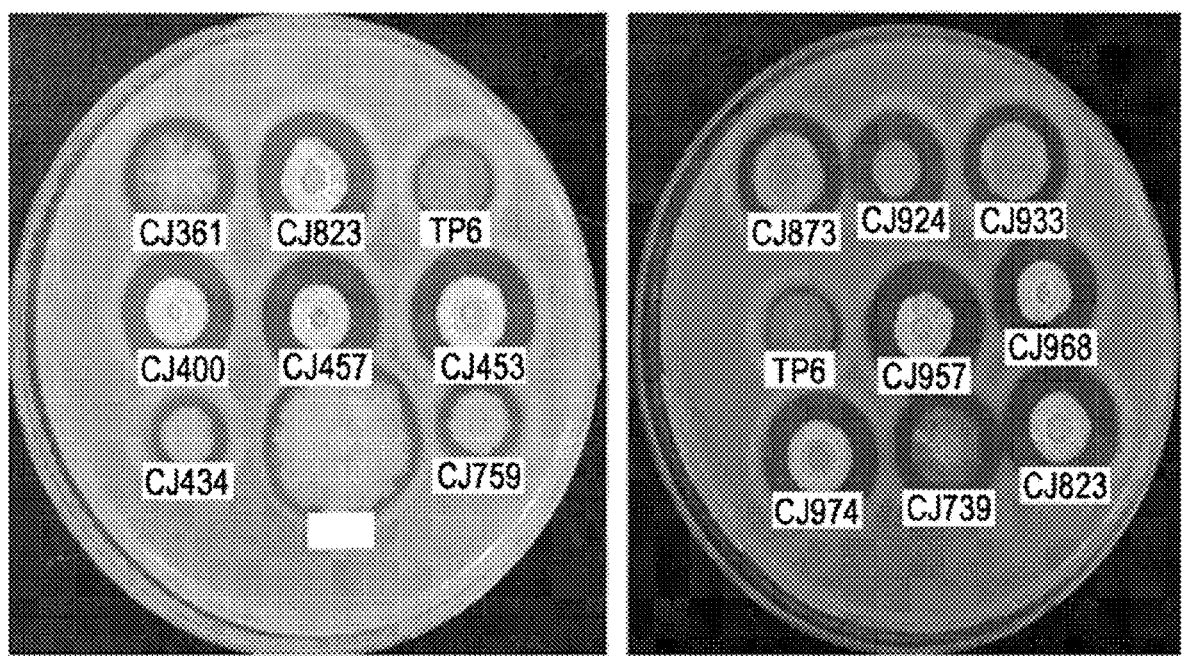
[FIG. 2]
S. typhymurium (ATCC14028)
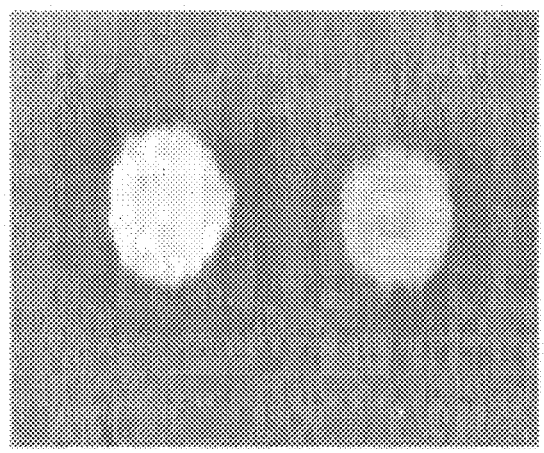
K2G    TP6
E. coli (KCCM11835)
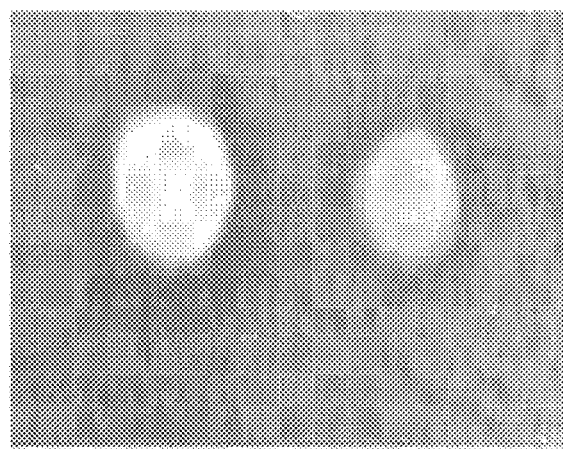
K2G    TP6

[FIG. 3]
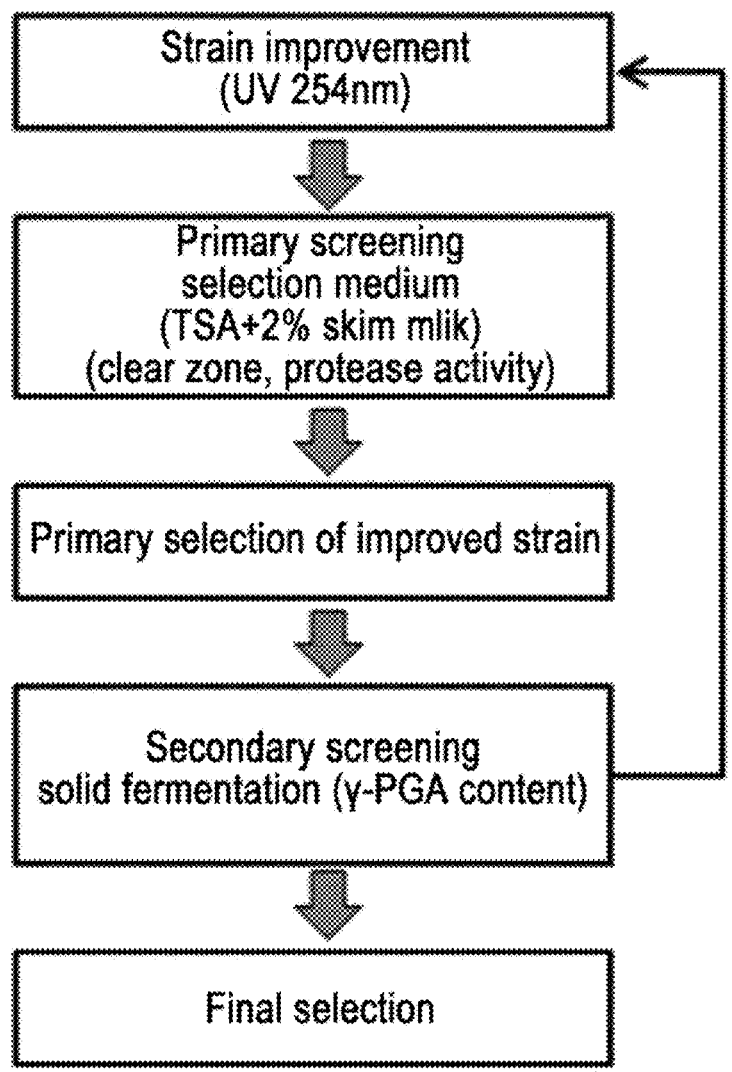
[FIG. 4]
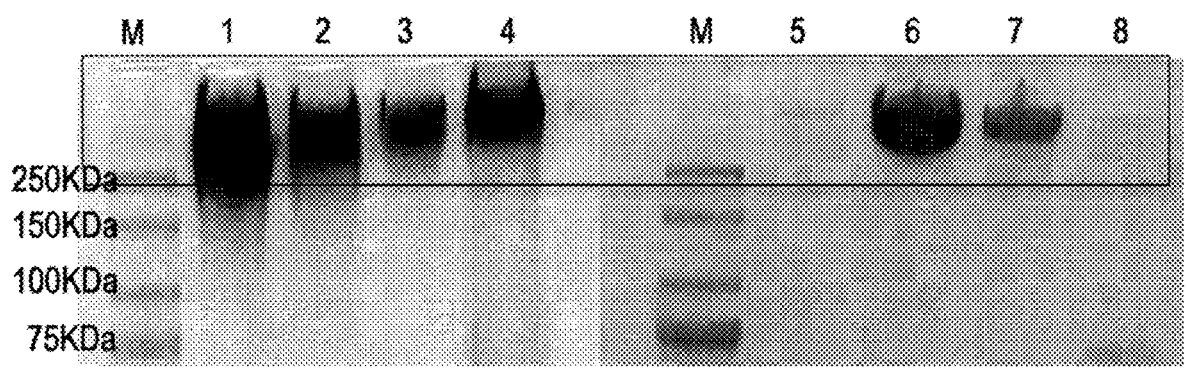

[FIG. 5]
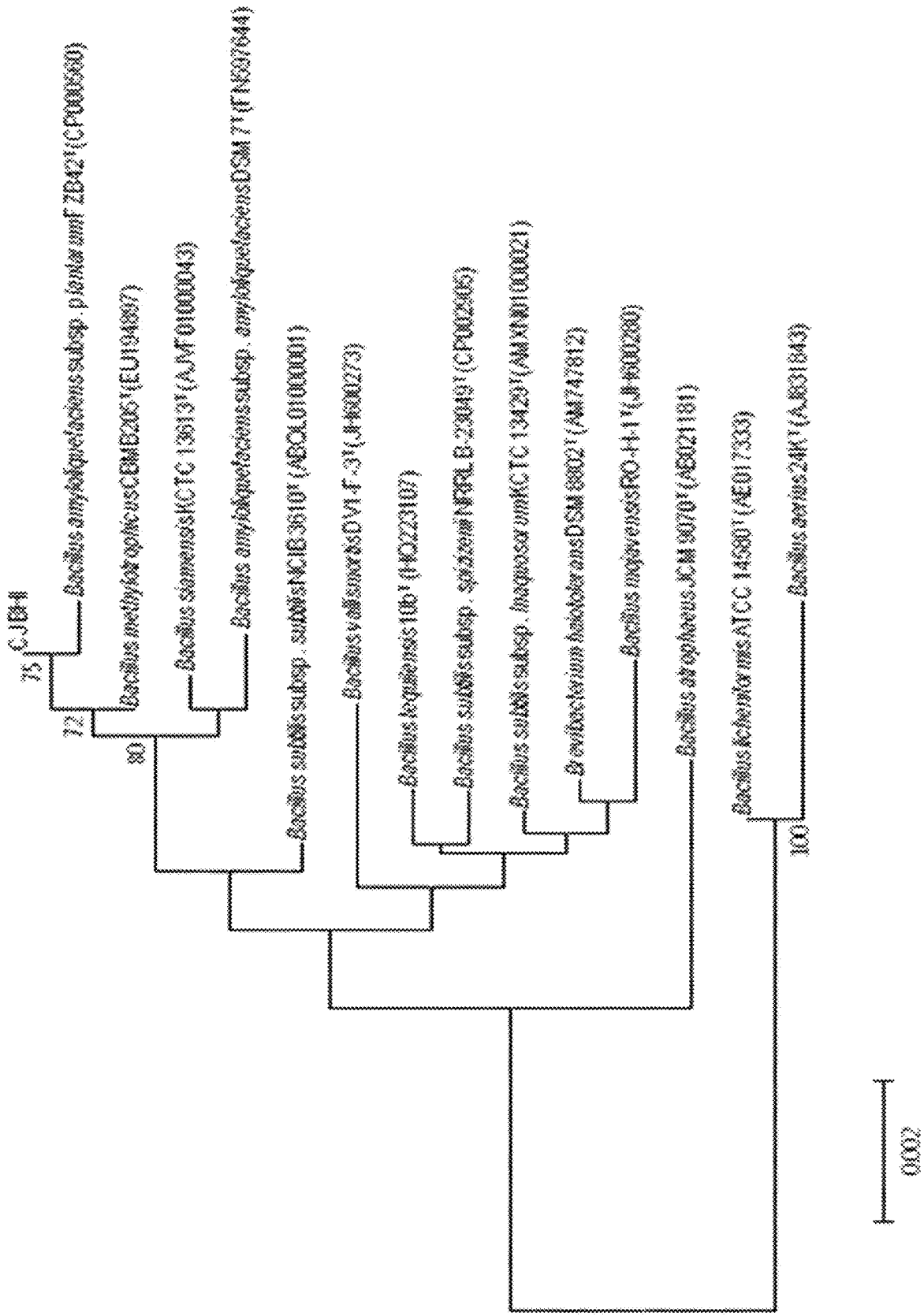

[FIG. 6]
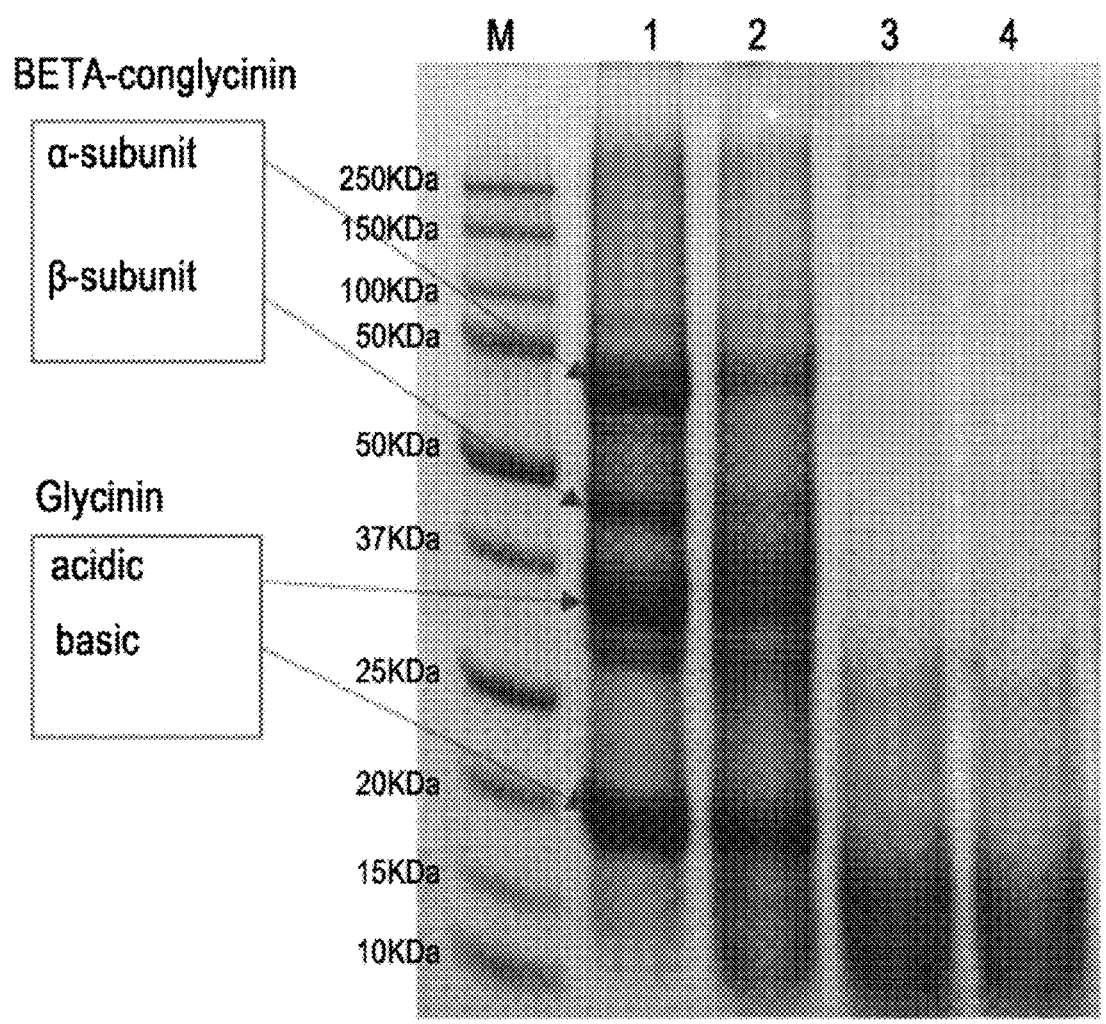

SEQUENCE LISTING

<160> NUMBER OF SEQ ID NOS: 3

<210> SEQ ID NO 1
<211> LENGTH: 1333
<212> TYPE: DNA
<213> ORGANISM: Bacillus amyloliquefaciens K2G
<220> FEATURE:
<223> OTHER INFORMATION: 16s rRNA

<400> SEQUENCE: 1

```
acgtgggtaa cctgcctgta agactgggat aactccggga aaccggggct aataccggat      60
ggttgtctga accgcatggt tcagacataa aaggtggctt cggctaccac ttacagatgg     120
acccgcggcg cattagctag ttggtgaggt aacggctcac caaggcgacg atgcgtagcc     180
gacctgagag ggtgatcggc cacactggga ctgagacacg gcccagactc ctacgggagg     240
cagcagtagg gaatcttccg caatggacga aagtctgacg gagcaacgcc gcgtgagtga     300
tgaaggtttt cggatcgtaa agctctgttg ttagggaaga acaagtgccg ttcaaatagg     360
gcggcacctt gacggtacct aaccagaaag ccacggctaa ctacgtgcca gcagccgcgg     420
taatacgtag gtggcaagcg ttgtccggaa ttattgggcg taaagggctc gcaggcggtt     480
tcttaagtct gatgtgaaag ccccggctc aaccggggag ggtcattgga aactggggaa      540
cttgagtgca aagaggaga gtggaattcc acgtgtagcg gtgaaatgcg tagagatgtg      600
gaggaacacc agtggcgaag gcgactctct ggtctgtaac tgacgctgag gagcgaaagc     660
gtggggagcg aacaggatta gataccctgg tagtccacgc cgtaaacgat gagtgctaag     720
tgttaggggg tttccgcccc ttagtgctgc agctaacgca ttaagcactc cgcctgggga     780
gtacggtcgc aagactgaaa ctcaaaggaa ttgacggggg cccgcacaag cggtggagca     840
tgtggtttaa ttcgaagcaa cgcgaagaac cttaccaggt cttgacatcc tctgacaatc     900
ctagagatag gacgtcccct tcgggggcag agtgacaggt ggtgcatggt tgtcgtcagc     960
tcgtgtcgtg agatgttggg ttaagtcccg caacgagcgc aacccttgat cttagttgcc    1020
agcattcagt tgggcactct aaggtgactg ccggtgacaa accggaggaa ggtggggatg    1080
acgtcaaatc atcatgcccc ttatgacctg gctacacacg tgctacaat ggacagaaca     1140
aagggcagcg aaaccgcgag gttaagccaa tcccacaaat ctgttctcag ttcggatcgc    1200
agtctgcaac tcgactgcgt gaagctggaa tcgctagtaa tcgcggatca gcatgccgcg    1260
gtgaatacgt tcccgggcct tgtacacacc gcccgtcaca ccacgagagt ttgtaacacc    1320
cgaagtcggt gag                                                        1333
```

<210> SEQ ID NO 2
<211> LENGTH: 20
<212> TYPE: DNA
<213> ORGANISM: Artificial Sequence
<220> FEATURE:
<223> OTHER INFORMATION: Universal primer 518F

<400> SEQUENCE: 2

```
ccagcagccg cggtaatacg                                                   20
```

<210> SEQ ID NO 3
<211> LENGTH: 18
<212> TYPE: DNA
<213> ORGANISM: Artificial Sequence
<220> FEATURE:
<223> OTHER INFORMATION: Universal primer 800R

```
<400> SEQUENCE: 3
taccagggta tctaatcc                                              18
```

BACILLUS SP. STRAIN WITH IMPROVED PRODUCTIVITY OF FERMENTED SOYBEAN MEAL AND METHOD FOR PRODUCING FERMENTED SOYBEAN MEAL USING THE SAME

CROSS-REFERENCE TO RELATED APPLICATIONS

This application is a § 371 national stage of PCT International Application No. PCT/KR2015/000900, filed Jan. 28, 2015, claiming priority of Korean Patent Application No. 10-2014-0010729, filed Jan. 28, 2014, the content of each of which is hereby incorporated by reference into the application.

REFERENCE TO SEQUENCE LISTING

This application incorporates-by-reference nucleotide and/or amino acid sequences which are present in the file named "161010_88763_Substitute_Sequence_Listing_CAE.txt" which is 2.68 kilobytes in size, and which was created Oct. 7, 2016 in the IBM-PC machine format, having an operating system compatibility with MS-Windows, which is contained in the text file filed Oct. 10, 2016 as part of this application.

TECHNICAL FIELD

The present invention relates to a novel *Bacillus* sp. strain with improved productivity of fermented soybean meal and a method for producing a fermented soybean meal using the same. More particularly, the present invention relates to a novel *Bacillus amyloliquefaciens* strain with improved productivity of fermented soybean meal, which is excellent in removal of anti-nutritional factors and in protease activity, and shows a high antimicrobial activity against pathogens and reduced productivity of viscous substances during fermentation, a method for producing a fermented soybean meal using the strain, a fermented soybean meal produced therefrom, and a feed composition including the same.

BACKGROUND ART

As diseases such as bovine spongiform encephalopathy, which have been fatal to human beings, are proven to be due to animal protein components added to a feed, there is a rapid global trend toward replacing animal proteins added to feed with vegetable proteins.

A defatted soybean meal (hereinbelow, referred to as "soybean meal") is the most common source of vegetable proteins used in feed markets as a substitute for animal proteins such as fish meal, meat bone powder or plasma. Soybean meal is also called soybean oil cake, which is a solid by-product resulting from extraction of soybean oil. In Korea, soybean meal, used as a vegetable protein source, accounts for 60% of total meal supply, reaching 2 million tons annually (Korea Feed Ingredients Association, 2004).

Soybean meal contains 55~56% by weight of proteins, 13~14% by weight of soluble carbohydrates, and 21~22% by weight of insoluble carbohydrates, based on the dry weight. In addition, soybean meal contains about 1% by weight of crude fat and about 4~6% by weight of lime (In-Kyu Han, Vegetable protein feed, Food Processing, Sun-Jin Publishing Co., 67-107, 1998).

Meanwhile, soybean meal contains a variety of anti-nutritional factors (ANFs), which can problematically impair the rate of digestion when used as a feed (Li et al. J. Anim. Sci., 68: 1790, 1990). Among them, a trypsin inhibitor (TI) is representative, and in terrestrial animals, dietary TI is known to interfere with the proper enzymatic functions of trypsin and chymotrypsin, leading to a reduction in the availability of total protein. In particular, since these anti-nutritional factors greatly affect young livestock, the use of soybean meal in the feed for young livestock is restricted. In addition, a red blood cell agglutinating substance, hemagglutinin, oligosaccharides causing diarrhea and abdominal pain in live stock, such as raffinose, stachyose, etc., or polysaccharides inhibiting nutrient absorption are known. Some of them are destroyed by heat treatment. However, during this process, soybean proteins are denatured and thus their solubility is reduced, and essential proteins such as lysine, etc., can be destroyed. Recently, for more efficient use of soybean proteins, processing methods for increasing efficiency by removing anti-nutritional factors have been developed.

The current processed soybean products, such as soy protein concentrates, isolated soy proteins, or hydrolyzed soy proteins, are usually produced by chemical treatment or enzymatic treatment. However, the chemical processing method is expensive, and causes a problem of decreasing the protein solubility, because denaturation of proteins or loss of soluble amino acids occurs due to heat treatment, chemical treatment, or heat drying during the production process. For this reason, heat treatment is performed, but does not cause extensive protein denaturation during the chemical processing method, and therefore, an anti-nutritional factor, trypsin inhibitor is considerably present in the soybean mill.

As a means for solving the problem of the chemical processing method, a fermented soybean meal product prepared by a biological processing method using *Bacillus* bacteria or fungi has been developed (Korean Patent Nos. 10-0645284, 10-0459240 and 10-0925173). This fermentation treatment processing method is used to remove a plurality of anti-nutritional factors and also to degrade proteins or carbohydrates into digestible low-molecular forms during the fermentation process, thereby producing high-quality protein materials for feed, which is excellent in digestion and absorption rate.

However, solid fermentation is generally used in the fermentation treatment processing method, and the solid fermentation has a disadvantage of continuously supplying air in order to maintain aerobic conditions and to remove fermentation heat produced during the fermentation process. In addition, the fermentation treatment processing method requires a long fermentation time of 48 hours or longer for removing the anti-nutritional factors above the optimum level. Such a long fermentation time reduces the turnover rate of the fermentor and causes an increase in the overall production cost.

Accordingly, the present inventors have developed a method for producing a fermented soybean meal by solid fermentation using a *Bacillus subtilis* TP6 strain (KFCC11343P, Accession No. KCCM11438P) having excellent characteristics required in the production of fermented soybean meal, in order to significantly shorten the fermentation time during the production of fermented soybean meal (Korean Patent Publication No. 10-2011-0027535). By this method, a fermented soybean meal having quality equivalent to or higher than the conventional fermented soybean meal can be produced even with a shorter fermentation time by using the *Bacillus subtilis* TP6 strain which is excellent in removal of anti-nutritional factors and in protease activity.

However, this method is problematic in that *Bacillus subtilis* TP6 strain has low ability to inhibit proliferation of pathogens and thus the pathogens are also proliferated during the fermentation when soybean meal is contaminated with *E. coli* or *Salmonella* during the fermentation.

Accordingly, the present inventors have made extensive efforts to select a fermentation strain having improved characteristics useful for solid fermentation of soybean meal. As a result, they have developed a *Bacillus amyloliquefaciens* K2G strain, which is excellent in removal of anti-nutritional factors, in protease activity, and in antimicrobial activity against pathogens, and has reduced productivity of viscous substances during fermentation. Further, the present inventors found that when the strain is used to perform solid fermentation of soybean meal, high-quality fermented soybean meal with improved digestion and absorption rates and feed efficiency can be produced due to low-molecularization by hydrolysis of soybean proteins and an increase in the content of crude proteins, inactivation of trypsin inhibitor, or a reduction in the content of anti-nutritional factors such as non-digestible polysaccharides even for a short fermentation time compared to the conventional method, thereby completing the present invention.

DISCLOSURE

Technical Problem

An object of the present invention is to provide a novel *Bacillus amyloliquefaciens* strain with improved productivity of fermented soybean meal.

Another object of the present invention is to provide a method for producing a fermented soybean meal by solid fermentation using the *Bacillus amyloliquefaciens* strain.

Still another object of the present invention is to provide a fermented soybean meal produced by the method.

Still another object of the present invention is to provide a feed composition including the fermented soybean meal.

Technical Solution

In one aspect to achieve the above objects, the present invention provides a novel *Bacillus amyloliquefaciens* K2G strain (KCCM11471P) useful for the production of fermented soybean meal by solid fermentation.

The *Bacillus amyloliquefaciens* K2G strain according to the present invention is characterized in that it is excellent in removal activity of anti-nutritional factors, in protease activity, and in antimicrobial activity against pathogens, and has reduced productivity of viscous substances during fermentation, thereby producing high-quality fermented soybean meal by solid fermentation.

Specifically, the *Bacillus amyloliquefaciens* K2G strain according to the present invention produces protease with a strong activity so as to inactivate various polysaccharide anti-nutritional factors such as trypsin inhibitor (TI) inhibiting digestion of soybean meal and to hydrolyze high-molecular weight soybean proteins into low-molecular weight proteins, thereby remarkably improving digestion and absorption rates of fermented soybean meal.

Further, while the *Bacillus amyloliquefaciens* K2G strain according to the present invention grows by utilizing carbohydrates among the components of soybean meal, it converts the carbohydrates into proteins constituting the cell. Thus, the relative content of crude proteins in fermented soybean meal is increased, which is an important factor in the production of high-quality feed.

In one preferred embodiment, the present inventors isolated 14 kinds of strains with excellent protease productivity from various traditional fermented foods, in order to select fermentation strains which can be used for the production of fermented soybean meal by solid fermentation (see Table 1).

From the isolated 14 kinds of strains, CJ823 strain was selected, in which the strain shows the most excellent antimicrobial activity against *E. coli* and *Salmonella* that are representative pathogens causing food poisoning in livestock.

The selected CJ823 strain shows remarkably excellent antimicrobial activity against *E. coli* and *Salmonella*, compared to *Bacillus subtilis* TP6 strain (KFCC 11343P; Korean Patent Publication No. 10-2011-0027535) which has been used as a fermentation strain in the conventional production method of fermented soybean meal by solid fermentation (see Table 2).

Further, it was confirmed that CJ823 strain effectively inhibits growth of *Salmonella* during practical fermentation process, and thus is suitable for the production of high-quality fermented soybean meal (see Table 3).

As such, CJ823 strain produces high concentration of protease and shows excellent antimicrobial activity against pathogens, but produces sticky viscous substances due to polymerization of levan form fructan and polyglutamate which are derived from sugars and proteins of the raw soybean by the enzymes produced during the fermentation process. Production of the viscous substances may cause problems in the control of fermentation process and transfer of fermented products upon mass-production of fermented soybean meal.

Accordingly, the present inventors caused UV-induced mutations in CJ823 strain in order to develop a mutant strain having reduced productivity of viscous substances while maintaining its own enzymatic/physiological characteristics (see FIG. 3).

First, CJ823 strain is exposed to 254 nm UV, and then 16 kinds of mutant strains are selected depending on the shape of colony and formation of clear zone due to production of viscous substances in a skim milk-containing selection medium. The selected 16 kinds of mutant strains are subjected to solid culture, and then protease activity and γ-PGA (Poly-γ-Glutamic Acid) content are analyzed to finally select a U304 mutant strain showing the highest protease activity and relatively low γ-PGAA content (see Table 4).

For identification of the finally-selected U304 mutant strain, its sugar assimilation was primarily analyzed. As a result, it was found that the U304 mutant strain has 98% similarity to *Bacillus subtilis* and *Bacillus amyloliquefaciens* in terms of biochemical characteristics (see Table 5).

Further, the results of 16S rRNA sequence analysis showed that the U304 mutant strain has 16S rRNA sequence of SEQ ID NO. 1. Based on this sequence, sequence homology and phylogenetic relationship between this strain and the known strains were analyzed. As a result, the U304 mutant strain showed 99.92% similarity to *Bacillus amyloliquefaciens* and the highest phylogenetic relationship therewith in the phylogenetic tree (see Table 5).

When the biochemical characteristics, sequence homology, and phylogenetic relationship were taken together, the U304 mutant strain according to the present invention was designated as *Bacillus amyloliquefaciens* K2G.

The *Bacillus amyloliquefaciens* K2G strain according to the present invention is an improved strain having reduced productivity of viscous substances by remarkably reducing production of polymers such as poly-γ-glutamic acid, while maintaining the characteristics of the parent strain, including high protease productivity and excellent antimicrobial activity against pathogens such as *E. coli* or *Salmonella*. Therefore, it can be very effectively used in the production of fermented soybean meal by solid fermentation.

In order to confirm the usefulness, changes in the crude protein content by solid fermentation of *Bacillus amyloliquefaciens* K2G strain according to the present invention were examined. As a result, it was found that soybean meal fermented by *Bacillus amyloliquefaciens* K2G strain according to the present invention showed the crude protein content equivalent to or higher than soybean meal fermented by *Bacillus subtilis* TP6 strain which is known as the conventional soybean meal fermentation strain, upon 24-hr fermentation (see Table 6).

Further, changes in the trypsin inhibitor (TI) content in soybean meal by fermentation of *Bacillus amyloliquefaciens* K2G strain according to the present invention were examined. As a result, it was found that the TI content in soybean meal fermented for 16 hours by *Bacillus amyloliquefaciens* K2G strain according to the present invention was equivalent to the TI content in soybean meal fermented for 24 hours by *Bacillus subtilis* TP6 strain, suggesting that the reduction in anti-nutritional factors can be achieved at an equivalent level by only 16-hr fermentation (see Table 7).

These results indicate that upon production of fermented soybean meal by solid fermentation, *Bacillus amyloliquefaciens* K2G strain according to the present invention is able to produce fermented soybean meal having a high content of the crude proteins and a low content of anti-nutritional factors as a high-quality protein feed for a short fermentation time, compared to the conventional strain. The present invention is excellent in that the reduced fermentation time increases the turnover rate of the fermentor to increase the number of batches annually producible, and consequently, consumers can be provided with high-quality fermented soybean meals at a lower cost.

Accordingly, the present inventors deposited *Bacillus amyloliquefaciens* K2G strain, which is excellent in removal activity of anti-nutritional factors, in protease activity and in antimicrobial activity against pathogens, and has reduced productivity of viscous substances so as to be useful for the production of high-quality fermented soybean meal by solid fermentation, under the Budapest Treaty to the Korea Culture Center of Microorganisms (KCCM) on Nov. 7, 2013 with Accession No. KCCM11471P.

In another aspect, the present invention provides a method for producing a fermented soybean meal by solid fermentation using *Bacillus amyloliquefaciens* K2G strain.

Specifically, the preparation method according to the present invention is characterized by including the steps of:

a) adding water to a soybean meal to perform heat-treatment;

b) cooling the heat-treated soybean meal, and then inoculating the *Bacillus amyloliquefaciens* K2G strain therein; and c) acquiring a fermented soybean meal by solid culture of the *Bacillus amyloliquefaciens* K2G strain inoculated in the soybean meal.

Step a) is a step of adding water to a soybean meal as a raw material to perform heat-treatment. Before solid fermentation, a proper amount of water is directly sprayed onto the raw soybean meal, and they are mixed to control the moisture content, followed by heat-treatment for a predetermined time.

According to one preferred embodiment of the present invention, the water in Step a) is added so that the water content in soybean meal is 30 to 80% (v/w), more preferably 30 to 70% (v/w), and more preferably 40 to 60% (v/w). Soybean meal having the water content within the above range is preferred in terms of prevention of fermentation delay due to low moisture, improvement of high costs required for transfer of soybean meal and drying process after fermentation, and heating efficiency.

Subsequently, the water-added soybean meal is subjected to heat-treatment. The heat-treatment is performed for the purpose of killing a variety of germs in the raw soybean meal, destruction of the soybean cell wall, and denaturation of proteins, thereby providing environment for active growth of the desired microorganism. The heat-treatment process can be performed by various methods known in the art, but steam or superheated steam is preferably used.

According to the preferred embodiment of the present invention, the heat-treatment of step a) is performed using steam of 70 to 130° C. for 10 to 60 minutes or superheated steam of 200 to 300° C. for a short time of several seconds to minutes, more preferably steam of 70 to 130° C. for 10 to 30 minutes, and most preferably steam of 80 to 121.1° C. for 10 to 30 minutes.

If the temperature of heat-treatment is low or the treatment time is short, there are problems that the sterilization effect on various germs is not sufficient or the subsequent fermentation process does not proceed smoothly. If the temperature of heat-treatment is high or the treatment time is long, protein denaturation occurs in the soybean meal to reduce the rate of digestion, resulting in deterioration of the quality of the final product. Therefore, it is preferable that the temperature and time of heat-treatment is adopted within acceptable ranges to avoid these problems.

Through the heat-treatment, it can be expected that the contaminants present in the soybean meal are almost completely removed, a chemical environment suitable for the subsequent solid fermentation is formed, and anti-nutritional factors such as trypsin inhibitor (TI) inhibiting the rate of digestion is slightly reduced.

Step b) is a step of cooling the heat-treated soybean meal to a temperature suitable for solid fermentation, and then inoculating the *Bacillus amyloliquefaciens* K2G strain therein. In the present invention, the cooling of soybean meal is ordinarily performed after heat-treatment, in which the cooling process can be readily performed through a transfer process using a cooling conveyor in order to prevent overheating and cool uniformly by increasing cooling rate.

According to the preferred embodiment of the present invention, the soybean meal in step b) is cooled to 30 to 50° C., more preferably 35 to 45° C., and more preferably 37° C.

After cooling the heat-treated soybean meal, it is preferable that the pre-culture media of *Bacillus amyloliquefaciens* K2G strain according to the present invention is uniformly inoculated into the prepared soybean meal medium as it is or by dilution with sterilized water.

The number of the fermentation strain inoculated into the heat-treated soybean meal is an important factor that influences the solid fermentation of soybean meal. The number of the fermentation strain immediately after inoculation into the heat-treated soybean meal is preferably $1 \times 10^5$ to $1 \times 10^9$ CFU/g.

If the inoculation amount is less than $1 \times 10^5$ CFU/g, a small amount of seed fermentation broth is needed, but there are disadvantages that much time is required for the fermentation of soybean meal to increase fermentation time needed for production and possibility of contamination. In contrast, if the inoculation amount is more than $1 \times 10^9$ CFU/g, the fermentation time can be considerably reduced, but there is a disadvantage that production of seed microorganisms used for inoculation is a troublesome issue. In particular, since fermentation performance is greatly influenced by growth characteristics of fermentation strain and type of fermentor, it is preferable that the inoculation amount is properly determined considering characteristics of the strain in the production step.

Step c) is a step of acquiring a fermented soybean meal by solid fermentation of the *Bacillus amyloliquefaciens* K2G strain inoculated in the soybean meal. For example, fermentation is performed using a packed-bed fermentor.

The packed-bed fermentor is divided into various types such as batch, closed, and continuous stirred tank reactor. The method of the present invention is not limited to any one of them, as long as it is useful for solid fermentation of soybean meal. Preferably, it can be selected depending on the production scale.

According to the preferred embodiment of the present invention, the *Bacillus amyloliquefaciens* K2G strain-inoculated soybean meal is applied to the packed-bed fermentor in a thickness of 5 to 50 cm, and fermented at 20 to 50° C. for 12 to 72 hours. At this time, it is preferable that the soybean meal-packed bed is thicker, and fermentation is performed at 30 to 45° C. for 12 to 48 hours. Most preferably, fermentation is performed at 37° C. for 24 hours.

The method of the present invention may further include the step of drying and pulverizing the fermented soybean meal at low temperature and moisture after Step c).

Water in the soybean meal is partially evaporated during the fermentation process, but the residual water content is as considerably high as 20 to 50% (v/w) immediately after fermentation. However, the preferable final water content of the fermented soybean meal product is 10 to 12% (v/w), and thus a drying process is required.

When solid fermentation is performed using *Bacillus amyloliquefaciens* K2G strain according to the present invention, the fermented soybean meal is in very good conditions, but conglomerates are slightly formed. Therefore, after the drying process, the process of pulverizing the fermented soybean meal is required to form a uniform particle size.

The drying and pulverization processes may be performed by various methods known in the art. However, when the drying process is excessively performed at a high temperature, a number of live bacteria in the fermented soybean meal may be killed, and thus it should be performed with caution. Preferably, the drying process is performed at a low temperature without killing living bacteria. Most preferably, the drying process is performed with hot air at low temperature and humidity. In the pulverization process, the fermented soybean meal may be pulverized to various sizes depending on the purpose of use, and preferably, by means of a hammer mill.

When solid fermentation of the soybean meal is performed using *amyloliquefaciens* K2G strain according to the above described method of the present invention, various anti-nutritional factors including TI in the soybean meal are reduced, the rate of digestion and absorption is improved by hydrolysis and low-molecularization of proteins, and the content of crude proteins is also increased, thereby improving the absolute value as feed. Consequently, it is highly valuable as a high-quality protein feed material being an alternative to animal proteins.

In still another aspect, the present invention provides a feed composition including the fermented soybean meal which is produced by the above method.

The content of the fermented soybean meal in the feed composition according to the present invention can be properly controlled depending on the kind and age of livestock to be applied, application form, desired effects, etc. For example, the content may be 1 to 99% by weight, preferably 10 to 90% by weight, and more preferably 20 to 80% by weight, but is not limited thereto.

For administration, the feed composition of the present invention may further include a mixture of one or more of an organic acid such as citric acid, fumaric acid, adipic acid, lactic acid, etc.; phosphate such as potassium phosphate, sodium phosphate, polyphosphate, etc.; a natural antioxidant such as polyphenol, catechin, tocopherol, vitamin C, green tea extract, chitosan, tannic acid, etc.; in addition to the fermented soybean meal. If necessary, other typical additive such as an anti-influenza agent, a buffer, a bacteriostatic agent, etc. may be added. Further, a diluent, a dispersing agent, a surfactant, a binder or a lubricant may be additionally added to formulate the composition into an injectable preparation such as an aqueous solution, a suspension, an emulsion, etc., a capsule, a granule, or a tablet.

Further, the feed composition of the present invention may be used together with various auxiliaries such as amino acids, inorganic salts, vitamins, an antioxidant, an antifungal agent, an antimicrobial agent, etc., a nutrient supplement, a growth accelerator, a digestion-absorption accelerator, and a prophylactic agent, in addition to the main ingredients including a vegetable protein feed such as pulverized or fragmented wheat, barley, corn, etc., an animal protein feed such as blood meal, meat meal, fish meal, etc., animal fat and vegetable oil.

When the feed composition of the present invention is used as a feed additive, the feed composition may be added as it is or used together with other components according to the typical method. The feed composition may be prepared in the administration form of an immediate release formulation or a sustained release formulation, in combination with non-toxic, pharmaceutically acceptable carriers. The edible carriers may be corn starch, lactose, sucrose, or propylene glycol. The solid carrier may be in the administration form of tablets, powders, troches, etc., and the liquid carrier may be in the administration form of syrups, liquid suspensions, emulsions, solutions, etc. Further, the administration agent may include a preservative, a lubricant, a solution accelerator, or a stabilizer, other agents for improving inflammatory diseases and a substance useful for the prevention of virus.

The feed composition of the present invention may be applied to an animal's diet, that is, feeds for many animals including mammals, poultry, fish and crustaceans. It may be used in commercially important mammals such as pigs, cattle, goats, etc., zoo animals such as elephants, camels, etc., livestock such as dogs, cats, etc. Commercially important poultry may include chickens, ducks, geese, etc., and commercially grown fish and crustaceans such as trout and shrimp may be also included.

The feed composition according to the present invention may be mixed in an amount of approximately 10 to 500 g, preferably 10 to 100 g per 1 kg, based on the dry weight of the livestock feed. After being completely mixed, the feed composition may be provided as mash, or may be further subjected to a pelletizing, extensification, or extrusion process, preferably.

Advantageous Effects

The *Bacillus amyloliquefaciens* K2G strain (KCCM11471P) according to the present invention is excellent in removal activity of anti-nutritional factors, in protease activity, and in antimicrobial activity against pathogens, and has reduced productivity of viscous substances during fermentation. Thus, when the strain is used as a seed microorganism to perform solid fermentation of soybean meal, high-quality fermented soybean meal with improved digestion and absorption rates and feed efficiency can be produced due to low-molecularization by hydrolysis of soybean proteins and an increase in the content of crude proteins, inactivation of trypsin inhibitors, or a reduction in the content of anti-nutritional factors such as non-digestible polysaccharides.

DESCRIPTION OF DRAWINGS

FIG. 1 shows the results of Example 1 for selecting strains with high protease productivity according to the present invention;

FIG. 2 shows the results of measuring growth inhibition activity of the strains with high protease productivity selected in Example 1 against that of *E. coli* and *Salmonella*;

FIG. 3 shows a flow chart for selecting a mutant strain with reduced productivity of viscous substances from the strains with high protease productivity according to the present invention;

FIG. 4 shows the results of concentration-gradient SDS-PAGE for qualitative analysis of γ-PGA content during the selection process of the mutant strain according to the present invention, in which
   Lane M: molecular weight marker
   Lane 1: 1 g/L γ-PGA standard
   Lane 2: 0.5 g/L γ-PGA standard
   Lane 3: 0.25 g/L γ-PGA standard
   Lane 4: CJ823 strain
   Lane 5: U304 mutant strain
   Lane 6: U305 mutant strain
   Lane 7: U306 mutant strain
   Lane 8: U307 mutant strain;

FIG. 5 is a phylogenetic tree showing the phylogenetic relationship of the mutant strain *Bacillus amyloliquefaciens* K2G selected according to the above procedures; and FIG. 6 shows the results of SDS-PAGE for hydrolysis degree of fermented soybean meal which is obtained by solid fermentation of *Bacillus amyloliquefaciens* K2G according to the present invention,
   Lane M: molecular weight marker
   Lane 1: raw material (raw soybean meal)
   Lane 2: TP6 fermentation for 20 hours
   Lane 3: K2G fermentation for 16 hours
   Lane 4: K2G fermentation for 20 hours.

MODE FOR INVENTION

Hereinafter, the present invention will be described in more detail with reference to Examples. However, it is apparent to those skilled in the art to which the present invention pertains that these Examples are for illustrative purposes only, and the scope of the present invention is not intended to be limited by these Examples.

Example 1: Selection of Strains Having High Protease Productivity

In order to isolate strains having excellent protease productivity, the present inventors isolated approximately 3000 kinds of microorganisms from a variety of traditional fermented foods (kimchi, fermented bean paste, traditional folk wine, salted fish, etc.), and of them, approximately 1300 kinds of feed adaptable (Korea Feed Ingredients Association, probiotics) *Bacillus* strains were identified. From the strains, it was intended to find multifunctional strains having high protease expression, an antimicrobial activity and a rapid growth rate.

In detail, selection of strains having high protease productivity was performed by comparing the size of clear zone which was formed due to degradation of substrate on 2% (w/v) skim milk (Difco, USA)-containing YM agar plate (yeast extract 3.0 g, malt extract 3.0 g, peptone 10.0 g, agar 20.0 g) (FIG. 1).

The strains having high protease productivity thus selected were inoculated in TSB media (enzymatic digest of casein 17.0 g, enzymatic digest of soybean meal 3.0 g, NaCl 5.0 g, dipotassium phosphate 2.5 g, dextrose 2.5 g, final pH: 7.3±0.2 at 25° C.), respectively, followed by culture at 37° C., and 200 rpm for 12 hours. Each 1.0 µl of the culture broths was spotted onto skim milk-containing YM agar plate. The agar plates were incubated at 37° C. for 16 hours and the diameter of the clear zone formed on the plate was measured.

At this time, *Bacillus subtilis* TP6 (KFCC 11343P) which has been used as a fermentation strain in the conventional method for producing fermented soybean meal by solid fermentation was used as a control group (Korean Patent Publication No. 10-2011-0027535).

TABLE 1

| Name of strain | Number of strain | Diameter of clear zone (mm) | Number of strain | Diameter of clear zone (mm) |
|---|---|---|---|---|
| *Bacillus* sp. | TP6 | 3.30 | CJ823 | 6.23 |
| | CJ361 | 5.46 | CJ873 | 5.48 |
| | CJ400 | 5.88 | CJ924 | 5.69 |
| | CJ434 | 5.34 | CJ933 | 5.20 |
| | CJ453 | 6.40 | CJ957 | 4.98 |
| | CJ457 | 6.10 | CJ968 | 4.87 |
| | CJ739 | 5.86 | CJ974 | 5.00 |
| | CJ759 | 5.43 | — | — |

As shown in Table 1, 14 kinds of strains were selected as strains having high protease productivity, and all of them showed higher protease activity than the *Bacillus subtilis* TP6.

Example 2: Isolation of Strains Having Inhibitory Activity on Proliferation of Pathogen In order to isolate strains capable of inhibiting growth or proliferation of *E. coli* and *Salmonella* which are the representative pathogens causing food poisoning in livestock and to develop *Salmonella*-free non-toxic products by applying the strains in the production of fermented soybean meal, 14 kinds of the strains having high protease productivity which were isolated in Example 1 were subjected to measurement of the antimicrobial activity against pathogens.

The antimicrobial activity against pathogens was measured by spot-on-the-lawn test on *Salmonella typhymurium* (ATCC14028) and *E. coli* (KCCM11835).

In detail, 14 kinds of the strains having high protease productivity were inoculated in GYP medium (glucose 10.0 g, yeast extract 8.0 g, polypeptone 2.0 g, pH 7.0), respectively, followed by liquid-culture at 37° C. and 180 rpm for 12 hours. Each 1.5 µl of the culture broths of the strains having high protease productivity was spotted onto GYP agar plate (glucose 10.0 g, yeast extract 8.0 g, polypeptone 2.0 g, agar 15.0 g, pH 7.0) to which each $1 \times 10^5$ CFU/ml of

*Salmonella typhymurium* ATCC14028 and *E. coli* ATCC11835 was added, followed by static culture at 37° C. for 15 hours. The size of inhibition zone which was formed around colonies of the strains having high protease productivity spotted onto the plate was examined to determine activity titer. The results are shown in the following Table 2. At this time, *Bacillus subtilis* TP6 was used as a control group.

TABLE 2

| Name of strain | Name of strain | E. coli (KCCM11835) | Salmonella typhymurium (ATCC14028) |
|---|---|---|---|
| Bacillus sp. | TP6 | + | ++ |
| | CJ361 | ++ | ++ |
| | CJ400 | ++ | ++ |
| | CJ434 | − | − |
| | CJ453 | − | − |
| | CJ457 | − | − |
| | CJ739 | +++ | ++ |
| | CJ759 | − | − |
| | CJ823 | ++++ | ++++ |
| | CJ873 | − | − |
| | CJ924 | +++ | ++ |
| | CJ933 | − | − |
| | CJ957 | − | − |
| | CJ968 | ++ | ++ |
| | CJ974 | +++ | + |

In Table 2, '−' or '+' is to determine the activity titer, based on the diameter of inhibition zone of live bacteria, and '−' indicates no antimicrobial or antimicrobial activity, '+' indicates that the diameter of inhibition zone is 10.05 mm or less, '++' indicates that the diameter of inhibition zone is 10.05 to 14.05 mm, '+++' indicates that the diameter of inhibition zone is 14.05 to 17.05 mm, and '++++' indicates that the diameter of inhibition zone is 17.05 mm or more.

Antimicrobial spectra of 14 kinds of the strains having high protease productivity against *Salmonella* and *E. coli* which are the most common causes of gastrointestinal disease in livestock were examined. As a result, CJ823 showed the most excellent antimicrobial power. The selected CJ823 showed remarkably high antimicrobial activity against both *E. coli* (++++ vs. +) and *Salmonella* (++++ vs. ++), compared to the control group *Bacillus subtilis* TP6.

Example 3: Test for Application of *Salmonella* Proliferation-Inhibiting Soybean Meal According to the results of Example 2, CJ823 on the agar plate showed excellent antimicrobial activity against *Salmonella*. However, the following experiment was performed in order to confirm whether the strain also exhibited the proliferation-inhibiting ability against *Salmonella* during practical fermentation of the soybean meal.

In detail, both CJ823 and *Salmonella typhymurium* ATCC14028 were inoculated into soybean meal (moisture content of 45%) which was steamed at 100° C. for 30 minutes, at a density of $4.5 \times 10^7$ CFU/g and $1.0 \times 10^3$ CFU/g, respectively and changes in the number of cells were examined at 37° C. and constant humidity for 24 hours. At this time, *Salmonella typhymurium* was singly inoculated into soybean meal, which was used as a control group. The mixture of *Salmonella typhymurium* and *Bacillus subtilis* TP6 was inoculated into soybean meal, which was used as a comparison group.

The strains were inoculated, and a predetermined amount of soybean meal was taken before fermentation and after fermentation for 12, 16 and 20 hours. The soybean meal was diluted in 0.8% NaCl sterile solution, and then each 100 μl thereof was applied to an XLD agar plate (yeast extract 3 g, lactose 7.5 g, sucrose 7.5 g, xylose 3.5 g, L-lysine 5 g, ferric ammonium citrate 0.8 g, Phenol Red 0.08 g NaCl 5 g, sodium deoxycholate 2.5 g, sodium thiosulfate 6.8 g, agar 13.5 g, final pH: 7.4±0.2 at 25° C.) to count the number of *Salmonella typhymurium* colony, and the results are shown in the following Table 3.

The ratio between two strains was measured on the assumption that *Salmonella typhymurium* contamination occurs during proliferation of the main fermentation strain CJ823 in the steamed soybean meal. Actual contamination ratio may differ depending on the environmental conditions for the production of fermented soybean meal.

TABLE 3

| | Number of *Salmonella typhymurium* (×10/g) | | |
|---|---|---|---|
| Fermentation time | Salmonella typhymurium alone | Salmonella typhymurium + TP6 | Salmonella typhymurium + CJ823 |
| 0 hr | 2330 | 2330 | 2330 |
| 12 hrs | 13900 | 2400 | 2000 |
| 16 hrs | 1200000 | 2300 | 50 |
| 20 hrs | 3100000 | 2200 | 35 |

As shown in Table 3, in the control group inoculated with only *Salmonella typhymurium*, as the culture time was increased, the number of the bacteria was steadily increased to $3.1 \times 10^7$ CFU/g after 20-hr fermentation. In contrast, in the comparison group inoculated with a mixture with *Bacillus subtilis* TP6, the number of *Salmonella typhymurium* was inhibited to $2.2 \times 10^4$ CFU/g. In the experimental group inoculated with the mixture with the CJ823 according to the present invention, the number of *Salmonella typhymurium* was further reduced to $3.5 \times 10^2$ CFU/g.

These results indicate that CJ823 according to the present invention effectively inhibits the growth of *Salmonella* during a practical fermentation process, and thus it is suitable for the production of high-quality fermented soybean meal.

Example 4: Selection of Mutant Strains

CJ823 selected in Examples 1 to 3 produces high concentration of protease and shows excellent antimicrobial activity against pathogens, but produces sticky viscous substances due to polymerization of levan form fructan and polyglutamate which are derived from sugars and proteins of the raw soybean by the enzymes produced during the fermentation process. Excessive production of the viscous substances in a large-scale industrial process hinders agitation, and there are difficulties in the control of dissolved oxygen in the fermented product and temperature, and transfer.

Accordingly, the present inventors caused UV-induced mutations in CJ823 strain as follows, in order to develop a mutant strain having reduced productivity of viscous substances while maintaining or improving its own enzymatic/physiological characteristics. The selection process of the mutant strain is as shown in FIG. 3.

First, CJ823 was plated on TSB agar plate (enzymatic digest of casein 17.0 g, enzymatic digest of soybean meal 3.0 g, NaCl 5.0 g, dipotassium phosphate 2.5 g, dextrose 2.5 g, agar 15.0 g, final pH: 7.3±0.2 at 25° C.) and cultured at 37° C. for 12 hours to activate the strain.

In this culture, 1% of a suspension of the seed microorganism was inoculated into TSB media (enzymatic digest of casein 17.0 g, enzymatic digest of soybean meal 3.0 g, NaCl 5.0 g, dipotassium phosphate 2.5 g, dextrose 2.5 g, final pH: 7.3±0.2 at 25° C.) prepared in advance, and cultured with shaking at 37° C. and 180 rpm. After culture, the culture broth was centrifuged at 25° C. and 8000 rpm for 10 minutes to separate the cell pellet and supernatant. Only the cell pellet was taken and washed with 0.8% NaCl sterile solution. After washing, artificial mutation was induced by UV irradiation (254 nm) to the recovered cell pellet using a UV lamp (VIBER LOURMAT, 115 V, 60 Hz).

The cell was plated on a 2% skim milk-containing TSA agar plate (enzymatic digest of casein 15 g, enzymatic digest of soybean meal 5 g, NaCl 5 g, agar 15 g, final pH 7.3±0.2 at 25° C.) which is a selection medium, and cultured at 37° C. for 20 hours. After culture, the size (diameter, mm) of clear zone formed was determined using Caliper (CD-20CPX, Mitutoyo, Kanagawa, Japan), and 16 kinds of mutant strains having a high proteolytic activity were primarily selected.

Subsequently, each of the 16 kinds of mutant strains thus selected was inoculated into heat-treated soybean meal, and cultured for 20 hours, and the culture broth obtained therefrom was centrifuged at 25° C. and 8000 rpm for 10 minutes to separate the cell pellet and supernatant. The γ-PGA content in the supernatant was determined by measuring the weight of γ-PGA which was recovered after isolation and purification and freeze-drying according to the method disclosed in the document (Goto et al. Biosci. Biotechnol. Biochem., 56:1031-1035, 1992).

The protease activity was measured according to the method described in Example 1, and the γ-PGA content was measured by the following two methods of qualitative and quantitative analysis.

First, for qualitative analysis of γ-PGA activity, 40 μl of the separated supernatant was mixed with 10 μl of 5× staining buffer solution, and then loaded on a 5 to 20% gradient SDS-polyamide gel to perform concentration gradient SDS-PAGE. After electrophoresis, the standard protein was stained with a Coomassie dye reagent, followed by destaining. Then, poly-γ-glutamic acid was stained with methylene blue to perform qualitative analysis.

As shown in FIG. 4, poly-γ-glutamic acid was detected in the supernatant of CJ823 (parent strain) of Lane 4, but the polymer-producing ability was greatly reduced and high protease activity was observed in the supernatant of U304 mutant strain of Lane 5.

Meanwhile, for quantitative analysis of γ-PGA content, the supernatant of solid fermentation was diluted with an equal amount of distilled water, and then centrifuged at 20,000×g for 20 minutes. pH of the obtained supernatant was adjusted to 3.0 using 6 M HCl, and left at 4° C. for one day. Thereafter, the supernatant was centrifuged at 25,000×g for 30 minutes, and then the pellet was recovered. The pellet was completely dissolved in 100-200 times volume of distilled water, and centrifuged at 25,000×g for 30 minutes to remove impurities. Salts were removed by dialysis at 4° C. for one day. The resultant was freeze-dried to recovery-PGA, and the results obtained therefrom are shown in the following Table 4.

TABLE 4

| Mutant strain | γ-PGA (g/L) | Protease (U/g) |
|---|---|---|
| TP6 | 1.61 | 150 |
| CJ823 | 25.36 | 450 |
| U101 | 11.19 | 330 |
| U102 | 13.36 | 220 |
| U103 | 14.83 | 320 |
| U304 | 4.96 | 500 |
| U305 | 24.50 | 400 |
| U306 | 16.70 | 280 |
| U307 | 5.52 | 120 |
| U609 | 6.13 | 15 |
| U610 | 11.09 | 450 |
| U611 | 21.77 | 260 |
| U612 | 12.05 | 400 |
| U813 | 10.12 | 180 |
| U814 | 23.13 | 370 |
| U815 | 1.06 | 260 |
| U816 | 5.26 | 100 |
| U1019 | 13.01 | 400 |

As shown in Table 4, most of the mutant strains showed low γ-PGA content, compared to CJ823. Of them, the U304 mutant strain showing the highest protease activity and relatively low γ-PGA content was finally selected. In particular, the U304 mutant strain showed lower γ-PGA content and three times or more higher protease activity than the control group, *Bacillus subtilis* TP6.

The finally selected U304 mutant strain is characterized in that it has reduced productivity of viscous substances by remarkably reducing production of polymers such as poly-γ-glutamic acid, while maintaining the characteristics of the parent strain, including production of high concentration of protease and excellent antimicrobial activity against pathogens.

Example 5: Determination of 16S rRNA Sequence of U304 Mutant Strain (K2G) and Phylogenetic Analysis In order to identify the U304 mutant strain having reduced productivity of viscous substances, the strain was inoculated into a new NA agar plate and cultured at 37° C. for 16 hours. The colonies formed were diluted with 0.8% NaCl sterile solution, and then injected into a BCL ID card (bioMNitek Inc., Hazewood, U.S.A.) consisting of 63 kinds of dry media and biochemical reactants, and the results were integrally stored in VITEK 2 Compact software (bioMVitek) every 15 minutes, and identification was completed after 14 hours.

As a universal primer for bacterial identification by 16S rRNA sequence analysis, 518F (5'-CCAGCAGCCGCGGTAATACG-3') and 800R (5'-TACCAGGGTATCTAATCC-3') of SEQ ID NOs. 2 and 3 were used, and after amplification of 16S rRNA by PCR, 1,333 bp containing a base sequence of 50~900 bp which is important in identification was translated using a BigDye Terminator v3.1 Cycle Sequencing kit (Applied Biosystems Inc., U.S.A.). The result of 16S rRNA sequence analysis showed that the U304 mutant strain has 16S rRNA sequence of SEQ ID NO. 1.

Sequence similarity was determined by Blast similarity search program (National Institute of Biotechnology Information) and the position was determined in a phylogenetic tree after multiple sequence alignment (FIG. 5).

TABLE 5

| Characteristics | Result | Characteristics | Result |
|---|---|---|---|
| β-Xylosidase | + | D-Mannitol | + |
| L-Lysine-arylamidase | − | D-Mannose | + |

TABLE 5-continued

| Characteristics | Result | Characteristics | Result |
|---|---|---|---|
| L-Aspartate arylamidase | – | D-Melezitose | – |
| Leucine arylamidase | (+) | N-Acetyl-D-glucosamine | – |
| Phenylalanine arylamidase | + | Palatinose | (+) |
| L-Proline arylamidase | – | L-Rhamnose | – |
| β-Galactosidase | – | β-Glucosidase | (+) |
| L-Pyrrolydonyl- arylamidase | + | β-Mannosidase | – |
| α-Galactosidase | + | Phosphoryl choline | – |
| Alanine arylamidase | + | Pyruvate | + |
| Tyrosine arylamidase | + | α-Glucosidase | – |
| β-N-Acetyl-glucosaminidase | (–) | D-Tagatose | – |
| Ala-Phe-Pro arylamidase | + | D-Trehalose | (+) |
| Cyclodextrine | – | Insulin | – |
| D-Galactose | – | D-Glucose | (+) |
| Glycogene | – | D-Ribose | – |
| myo-Inositol | – | Putrescine assimilation | – |
| Methyl-A-D-glucopyranoside acidification | + | Kanamycin resistance | (–) |
| Ellman | – | Oleandomycin resistance | – |
| Methyl-D-xylosdie | – | Esculin hydrolyse | + |
| α-Mannosidase | – | Tetrazolium Red | – |
| MALTOTRIOSE | – | Plomixin_B resistance | – |
| Glycine ARYLAMIDASE | (–) | | |

The results of 63 kinds of biochemical tests were analyzed by Vitec 2 Compact Software. As a result, the strain was classified as *Bacillus subtilis/Bacillus amyloliquefaciens* with a probability of 98%. As shown in FIG. 5, the results of phylogenetic analysis showed that U304 mutant strain has the closest relationship with the standard strain, *Bacillus amyloliquefaciens* subsp. *plantarum* FZB42T (CP000560) and 16S rDNA sequence homology was 99.92% (1332 bp/1333 bp).

Therefore, when the biochemical characteristics and the results of the phylogenetic analysis were taken together, the U304 mutant strain according to the present invention was designated as *Bacillus amyloliquefaciens* K2G, and deposited under Budapest Treaty to the Korea Culture Center of Microorganisms (KCCM) on Nov. 7, 2013 with Accession No. KCCM11471P.

Example 6: Changes in Crude Protein Content According to Fermentation Time Upon Fermentation of Soybean Meal Using *Bacillus amyloliquefaciens* K2G In order to examine changes in the crude protein content according to fermentation time upon fermentation of soybean meal using *Bacillus amyloliquefaciens* K2G according to the present invention, the following experiment was performed.

First, 400 g of soybean meal was prepared to have the water content of 45%, and steamed at 100° C. for 30 minutes, and then cooled to 40° C. or lower. Subsequently, the *Bacillus amyloliquefaciens* K2G was plated on TSB agar plate (enzymatic digest of casein 17.0 g, enzymatic digest of soybean meal 3.0 g, NaCl 5.0 g, dipotassium phosphate 2.5 g, dextrose 2.5 g, agar 15.0 g, final pH: 7.3±0.2 at 25° C.), and cultured at 37° C. for 12 hours to activate the strain. Approximately 2 loops of the activated strain was suspended in 9 ml of 0.8% NaCl sterile solution (diluted to 0.2 at $A_{660nm}$), and this suspension was used as a seed microorganism. In this culture, 1% of the suspension of the seed microorganism was inoculated into 40 ml of TSB media (enzymatic digest of casein 17.0 g, enzymatic digest of soybean meal 3.0 g, NaCl 5.0 g, dipotassium phosphate 2.5 g, dextrose 2.5 g, final pH: 7.3±0.2 at 25° C.) prepared in advance, and cultured with shaking at 37° C. and 180 rpm.

40 ml of the culture broth of the *Bacillus amyloliquefaciens* K2G was prepared to have the water content of 45%, added to the steamed soybean meal, and mixed well, followed by static culture at 37° C. and constant humidity for 20 hours. The culture sample was dried in a 60° C. dryer until the water content reached 10% or less, and then the crude protein content in each sample was measured using a Kjeldahl system (Kjltec 2100). At this time, the crude protein content was measured before fermentation and after fermentation for 12, 16 and 20 hours, and *Bacillus subtilis* TP6 was used as a control group. The crude protein content (%, correction to 10% moisture) measured therefrom is shown in the following Table 6. At this time, *Bacillus subtilis* TP6 was used as a control group.

TABLE 6

| Section | TP6 (%, correction to 10% moisture) | K2G (%, correction to 10% moisture) |
|---|---|---|
| Raw soybean meal | 50.86 ± 0.15 | 50.86 ± 0.15 |
| Steamed soybean meal | 50.91 ± 0.12 | 50.91 ± 0.12 |
| 0-hr fermentation | 51.19 ± 0.38 | 51.19 ± 0.38 |
| 12-hr fermentation | 54.21 ± 1.18 | 55.59 ± 0.66 |
| 16-hr fermentation | 55.07 ± 0.79 | 56.46 ± 0.19 |
| 20-hr fermentation | 55.86 ± 0.75 | 57.32 ± 0.28 |
| 24-hr fermentation | 56.36 ± 0.80 | 58.02 ± 0.45 |

As shown in Table 6, based on 24-hr fermentation, the soybean meal fermented by *Bacillus amyloliquefaciens* K2G according to the present invention showed the crude protein content equivalent to or higher than the soybean meal fermented by *Bacillus subtilis* TP6 which is known as the conventional soybean meal fermentation strain.

These results indicate that *Bacillus amyloliquefaciens* K2G according to the present invention can be effectively used in the production of fermented soybean meal as a high-quality protein feed.

Example 7: Changes in TI Content According to Fermentation Time Upon Fermentation of Soybean Meal Using *Bacillus amyloliquefaciens* K2G In order to examine changes in the trypsin inhibitor (TI) content according to fermentation time upon fermentation of soybean meal using *Bacillus amyloliquefaciens* K2G according to the present invention, the following experiment was performed.

Specifically, as in Example 6, 400 g of soybean meal was prepared to have the water content of 45%, and steamed at 100° C. for 30 minutes, and then *Bacillus amyloliquefaciens* K2G was inoculated into the steamed soybean meal at a density of 4.5×10⁷ CFU/ml, followed by culture at 37° C. and constant humidity for 24 hours. The TI content was measured according to AACC-71-10 (American association of cereal chemists, 1995) before fermentation and after fermentation for 16, 20 and 24 hours, and the TI content (mg/g) measured therefrom is shown in the following Table 7. At this time, *Bacillus subtilis* TP6 was used as a control group.

TABLE 7

| Section | TP6 (TI, mg/g) | K2G (TI, mg/g) |
|---|---|---|
| Raw soybean meal | 4~5 | 4~5 |
| Steamed soybean meal | 2~2.5 | 2~2.5 |
| 16-hr fermentation | 1.26 | 0.39 |

TABLE 7-continued

| Section | TP6 (TI, mg/g) | K2G (TI, mg/g) |
| --- | --- | --- |
| 20-hr fermentation | 0.53 | 0.00 |
| 24-hr fermentation | 0.38 | 0.00 |

As shown in Table 7, the soybean meal fermented by *Bacillus amyloliquefaciens* K2G according to the present invention showed TI content of 0.39 mg/g after 16-hr fermentation, which corresponds to that in the soybean meal fermented for 24 hours by *Bacillus subtilis* TP6 which is known as the conventional soybean meal fermentation strain, suggesting that the reduction in anti-nutritional factors can be achieved at an equivalent level by only 16-hr fermentation.

The present invention is excellent in that the reduction in fermentation time increases the turnover rate of the fermentor to increase the number of batches annually producible, and consequently, consumers can be provided with high-quality fermented soybean meals at a lower cost.

Example 8: Measurement of Hydrolysis Degree of Soybean Protein and its Solubility in KOH Upon Fermentation of Soybean Meal Using *Bacillus amyloliquefaciens* K2G Soybean meal is a vegetable feed raw material having high content of proteins, but has a disadvantage that it is insufficient for, in particular, young livestock, due to anti-nutritional factors and proteins having a low digestion and absorption rate. One of methods for improving this disadvantage is to prepare the proteins in the form of hydrolyzed peptides or to degrade it into low-molecular weight proteins being easily digestible by fermentation using a microorganism. *Bacillus amyloliquefaciens* K2G according to the present invention is a strain having high protease productivity, and thus it was expected that soybean proteins in the fermented soybean meal prepared by using the same can be degraded by protease secreted from the strain.

In order to confirm this, the hydrolysis degree of the fermented soybean meal according to the present invention was first measured. As in Example 6, 400 g of soybean meal was prepared to have the water content of 45%, and steamed at 100° C. for 30 minutes, and then *Bacillus amyloliquefaciens* K2G was inoculated into the steamed soybean meal at a density of $4.5 \times 10^7$ CFU/ml, followed by culture at 37° C. and constant humidity for 24 hours. The culture broth obtained therefrom was centrifuged at 25° C. and 8000 rpm for 10 minutes to separate the cell pellet and supernatant. 40 µl of the separated supernatant was mixed with 10 µl of 5× staining buffer solution, and then SDS-PAGE (10%) was performed to examine migration of the proteins according to their molecular weight. After electrophoresis, the polyamide gel was stained with Coomassie Brilliant R250 to examine the composition and molecular weight of the protein, and the results are shown in FIG. 6. At this time, raw soybean meal and fermented soybean meal prepared by *Bacillus subtilis* TP6 were used as control groups.

As shown in FIG. 6, it was found that the fermented soybean meal prepared by *Bacillus amyloliquefaciens* K2G according to the present invention showed a high protein density in the low molecular weight region, compared to the raw soybean meal and the fermented soybean meal prepared by another strain. On SDS-polyamide gel, upper bands indicate high-molecular weight proteins and lower bands indicate low-molecular weight proteins. These results indicate that in the case of soybean meals having the same molecular weights, high-molecular weight proteins in the soybean meal fermented by *Bacillus amyloliquefaciens* K2G according to the present invention are hydrolyzed into low-molecular weight proteins.

According to the previous reports, dietary supplementation of broiler chickens was performed four times using the soybean meal showing KOH (potassium hydroxide) solubility of 80% and the soybean meal showing lower solubility (55% to 68%). As a result, the weight, feed intake, and feed efficiency of broiler chickens which were fed with the soybean meal showing low KOH solubility were remarkably low or decreased, compared to the broiler chickens fed with the soybean meal showing KOH solubility of 80% (Abulto et al. J. Appl. Poult. Res. 7:189-195, 1998b).

Therefore, KOH solubility of the fermented soybean meal according to the present invention was measured according to the method disclosed in the document (Parsons et al. J Anim Sci., 69: 2918-24, 1991). Briefly, 1.0 g of the fermented soybean meal thus prepared was added to 0.2% KOH solution and mixed for 20 minutes, followed by filtration. The nitrogen content in the filtrate was measured using a Kjeldahl system and converted to solubility. The results are shown in Table 8.

TABLE 8

| Section | TP6 (KOH, %) | K2G (KOH, %) |
| --- | --- | --- |
| Raw soybean meal | 80.17 ± 2.38 | 80.17 ± 2.38 |
| Steamed soybean meal | 73.35 ± 3.32 | 73.35 ± 3.32 |
| 16 hr-fermentation | 78.38 ± 2.85 | 85.03 ± 3.07 |
| 24 hr-fermentation | 78.99 ± 3.01 | 85.20 ± 3.60 |

As shown in Table 8, KOH solubility of the steamed soybean meal was reduced from 80% to 70%, but KOH solubility was increased to 85% during solid fermentation by *Bacillus amyloliquefaciens* K2G according to the present invention. These results suggest that KOH was increased due to degradation of soybean proteins by protease secreted from *Bacillus amyloliquefaciens* K2G according to the present invention.

INDUSTRIAL APPLICABILITY

The *Bacillus amyloliquefaciens* K2G strain (KCCM11471P) according to the present invention is excellent in removal activity of anti-nutritional factors, in protease activity, and in antimicrobial activity against pathogens, and has reduced productivity of viscous substances during fermentation. Thus, when the strain is used as a seed microorganism to perform solid fermentation of soybean meal, high-quality fermented soybean meal with improved digestion and absorption rates and feed efficiency can be produced due to low-molecularization by hydrolysis of soybean proteins and an increase in the content of crude proteins, inactivation of trypsin inhibitors, or a reduction in the content of anti-nutritional factors such as non-digestible polysaccharides.

What is claimed is:

1. A method for producing a fermented soybean meal by solid state fermentation, comprising inoculating *Bacillus amyloliquefaciens* strain K2G (Korean Culture Center of Microorganisms Accession No. KCCM11471P) into a soybean meal, and fermenting the soybean meal.

2. The method according to claim 1, comprising the steps of:
   a) adding water to a soybean meal and then performing heat-treatment of the soybean meal;
   b) cooling the heat-treated soybean meal and inoculating the *Bacillus amyloliquefaciens* K2G strain into the cooled soybean meal; and
   c) obtaining a fermented soybean meal by solid state culturing of the *Bacillus amyloliquefaciens* K2G strain in the soybean meal.

3. The method according to claim 2, wherein the heat-treated soybean meal in Step a) has a water content of 30 to 80% (w/v).

4. The method according to claim 2, wherein the heat treatment of Step a) is carried out by heating soybean meal at a temperature of 70 to 130° C. for 10 to 30 minutes.

5. The method according to claim 2, wherein the soybean meal in Step b) is cooled to a temperature of 30 to 50° C.

6. The method according to claim 2, wherein the number of *Bacillus amyloliquefaciens* K2G strain immediately after inoculation in Step b) is in a range of $1 \times 10^5$ to $1 \times 10^9$ CFU/g.

7. The method according to claim 2, wherein the solid state culture in Step c) is performed at a temperature of 30 to 45° C. for 12 to 48 hours.

8. The method according to claim 2, further comprising the step of drying and pulverizing the fermented soybean meal obtained in Step c).

* * * * *